(12) United States Patent
Liang et al.

(10) Patent No.: US 9,268,337 B2
(45) Date of Patent: Feb. 23, 2016

(54) ON-LINE DETECTION OF ORGANIC CONTAMINANT IN CONDENSATE SYSTEM OF SUGAR PRODUCTION PROCESSES USING FLUORESCENCE TECHNOLOGY

(75) Inventors: Ling Liang, Shanghai (CN); Patrick P. Chen, Shanghai (CN); Rodney H. Banks, Aurora, IL (US); Michael W. Willer, Aurora, IL (US); Narasimha M. Rao, Naperville, IL (US)

(73) Assignee: Ecolab USA Inc., Naperville, IL (US)

( * ) Notice: Subject to any disclaimer, the term of this patent is extended or adjusted under 35 U.S.C. 154(b) by 321 days.

(21) Appl. No.: 13/880,651

(22) PCT Filed: Oct. 3, 2011

(86) PCT No.: PCT/US2011/054572
§ 371 (c)(1),
(2), (4) Date: Oct. 17, 2013

(87) PCT Pub. No.: WO2012/054220
PCT Pub. Date: Apr. 26, 2012

(65) Prior Publication Data
US 2014/0060659 A1    Mar. 6, 2014

(30) Foreign Application Priority Data

Oct. 20, 2010  (CN) .......................... 2010 1 0522876

(51) Int. Cl.
| | |
|---|---|
| G01N 21/64 | (2006.01) |
| G05D 7/00 | (2006.01) |
| G01N 21/85 | (2006.01) |
| G01N 33/18 | (2006.01) |
| G01N 21/94 | (2006.01) |
| G01N 21/84 | (2006.01) |

(52) U.S. Cl.
CPC .............. *G05D 7/00* (2013.01); *G01N 21/6486* (2013.01); *G01N 21/85* (2013.01); *G01N 33/1826* (2013.01); *G01N 21/94* (2013.01); *G01N 2021/8411* (2013.01); *Y10T 137/0324* (2015.04)

(58) Field of Classification Search
CPC .................. G01N 2021/8411; G01N 21/6486; G01N 21/85; G01N 21/94; G01N 33/1826; Y10T 137/0324
USPC ......................................... 436/55, 172; 137/2
See application file for complete search history.

(56) References Cited

U.S. PATENT DOCUMENTS

| | | |
|---|---|---|
| 5,304,800 A | 4/1994 | Hoots et al. |
| 5,389,548 A | 2/1995 | Pierce et al. |
| 5,411,889 A | 5/1995 | Godfrey et al. |

(Continued)

FOREIGN PATENT DOCUMENTS

| | | |
|---|---|---|
| CN | 1130700 A | 9/1996 |
| CN | 2720434 Y | 8/2005 |

(Continued)

*Primary Examiner* — William McCalister
(74) *Attorney, Agent, or Firm* — Leydig, Voit & Mayer, Ltd.

(57) ABSTRACT

A method of measuring contamination in fluid that is expelled from a food processing system is presented. The method of measuring is carried out with fluorescence. The fluid is typically allowed to enter into an energy transfer system, but if the contamination exceeds a certain level, the fluid should be prevented from entering the energy transfer system. The fluid is generally comprised of water expelled from a sugar processing operation.

13 Claims, 2 Drawing Sheets

Results from Field Test 1 in Example 2.

(56) References Cited

U.S. PATENT DOCUMENTS

| | | | |
|---|---|---|---|
| 5,416,323 A | 5/1995 | Hoots et al. | |
| 5,435,969 A | 7/1995 | Godfrey et al. | |
| 5,658,798 A | 8/1997 | Bertin et al. | |
| 6,013,228 A * | 1/2000 | Achter | B07C 5/34 209/3.1 |
| 6,166,366 A * | 12/2000 | Lewis | G01N 21/89 250/208.1 |
| 6,255,118 B1 | 7/2001 | Rao et al. | |
| 6,885,440 B2 | 4/2005 | Silcott et al. | |
| 6,902,935 B2 * | 6/2005 | Kaufman | A61B 1/00009 436/164 |
| 7,436,515 B2 | 10/2008 | Kaye et al. | |
| 7,989,780 B2 | 8/2011 | Tokhtuev et al. | |
| 2003/0098422 A1 | 5/2003 | Silcott et al. | |
| 2005/0070025 A1 | 3/2005 | Mooradian et al. | |
| 2006/0237665 A1 * | 10/2006 | Barney | G01N 15/1459 250/458.1 |
| 2006/0250606 A1 | 11/2006 | Kaye et al. | |
| 2008/0293153 A1 * | 11/2008 | Kutateladze | B82Y 30/00 436/166 |
| 2009/0293646 A1 | 12/2009 | Johnson et al. | |
| 2010/0084572 A1 | 4/2010 | Tokhtuev et al. | |

FOREIGN PATENT DOCUMENTS

| | | |
|---|---|---|
| CN | 101184987 A | 5/2008 |
| CN | 101189520 A | 5/2008 |

* cited by examiner

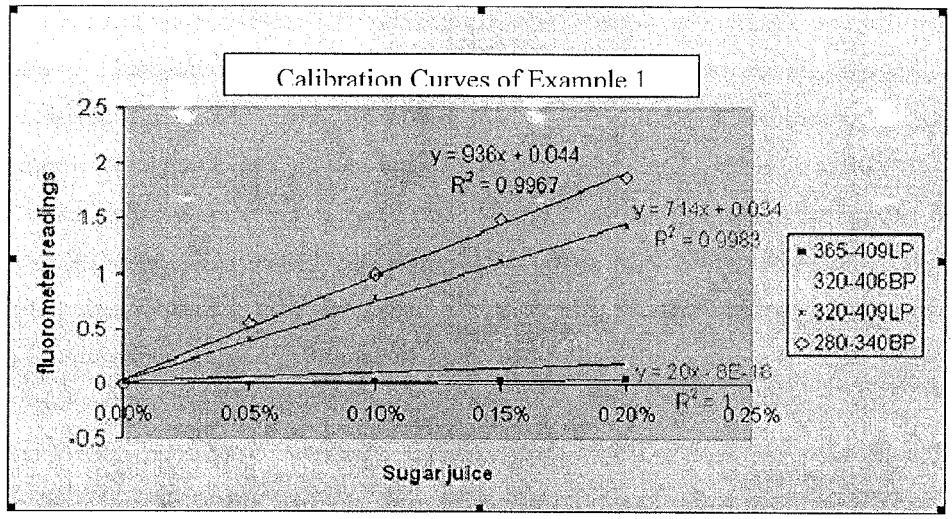
FIG. 1: Results from Example 1.
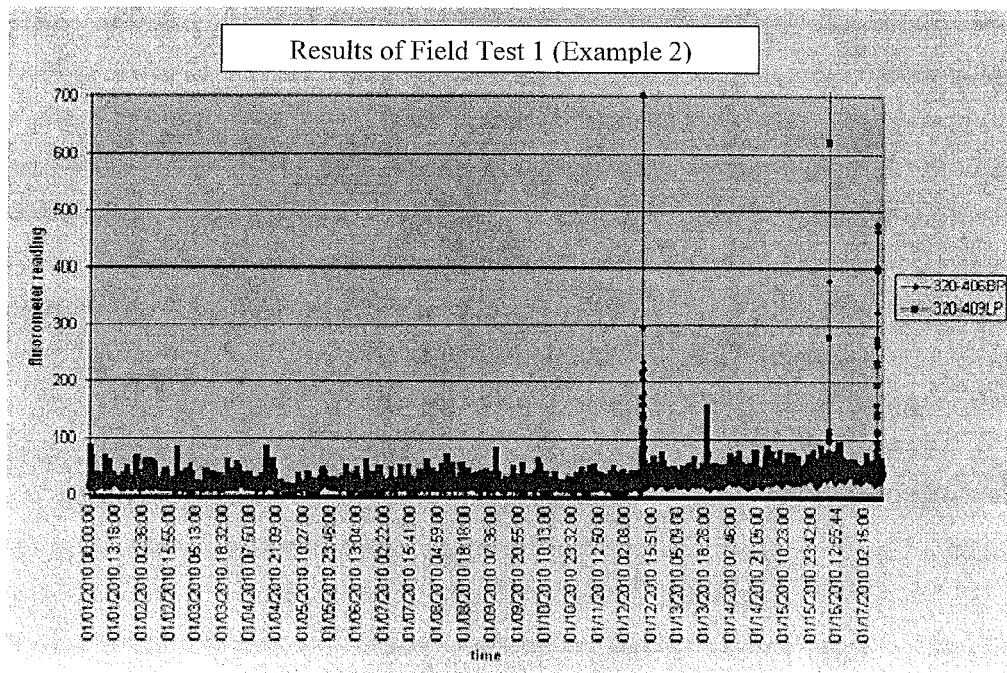
FIG. 2: Results from Field Test 1 in Example 2.

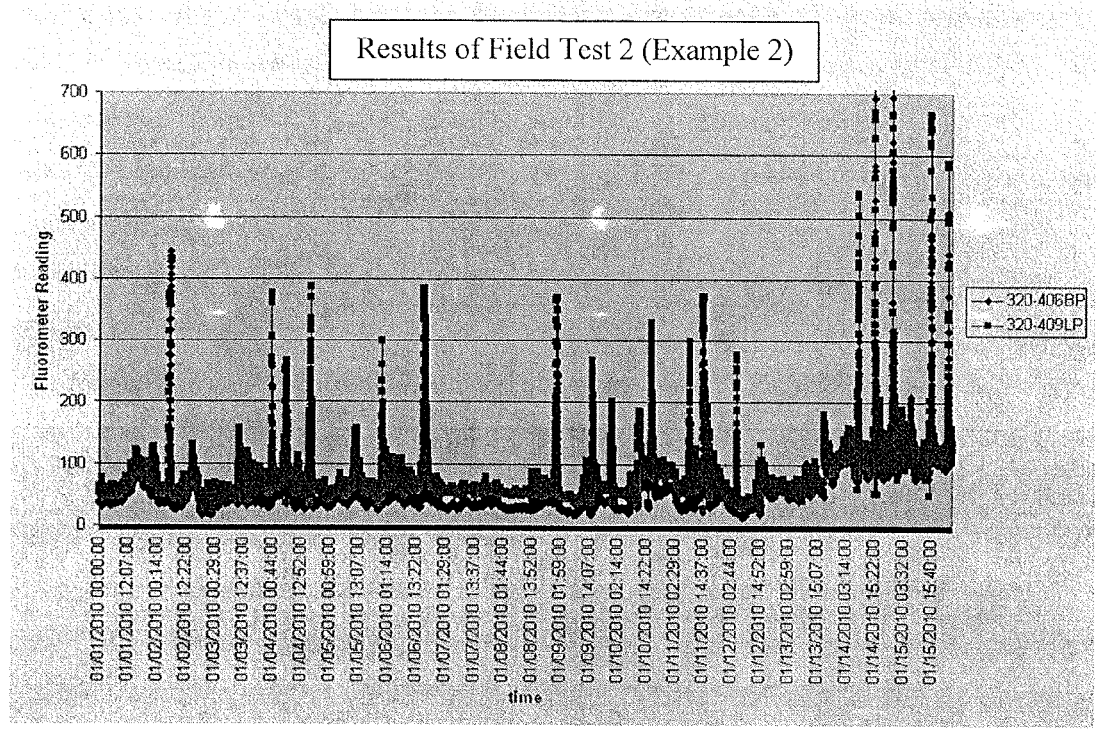
FIG. 3: Results from Field Test 2 in Example 2.

ON-LINE DETECTION OF ORGANIC CONTAMINANT IN CONDENSATE SYSTEM OF SUGAR PRODUCTION PROCESSES USING FLUORESCENCE TECHNOLOGY

FIELD OF THE INVENTION

The invention is a method of measuring impurities in a fluid and preventing contamination of energy transfer fluid. The fluid is expelled from a process and can be used to feed an energy transfer system.

BACKGROUND

The food processing industry employs vast quantities of water to create purified food products. Among the food industries with high volumes of water requirements are the sugar cane processing, sugar beet processing, fruit and vegetable processing, meat and poultry processing, grain processing, fat and oil processing, and dairy product processing industries. Unit operations that are most common to the various types of food processing listed above include energy transfer systems, particularly boiler systems. Boiler systems have a high demand for make-up water. Particularly in sugar processing, the expelled fluid is typically warmer than ordinary tap water, providing an ideal feed source for a heat-adding energy transfer system such as a boiler system.

Much of the fluid expelled from food processing plants is water and can be re-used in processing operations if it is sufficiently pure. Impurities in the expelled fluid can cause significant problems in an energy transfer system and must be monitored. To prevent these impurities from entering the energy transfer system, it is important to first detect those impurities present in the fluid that is expelled from a food processing stream. If the impurities become concentrated over a certain level, the expelled fluid should be prevented from entering the energy transfer system.

The problems associated with the recycling the expelled fluid for energy transfer systems, particularly boiler systems, may be taken as exemplary in the evaluation of the need for efficient methods for detection of impurities in the fluid expelled from food processing systems. Boiler system feed water, which normally is comprised of both makeup water and recirculated condensate water, contains some impurities regardless of the extent to which such waters are treated before being fed to a boiler. When steam is generated, substantially pure water vapor is discharged from the boiler leaving the impurities (the dissolved and suspended solids) behind, which results in the increase of their concentration in the boiler water. The discharged steam is replaced by contaminant-containing feedwater. An ever increasing concentration of dissolved and suspended solids in the boiler water inevitably results in very serious problems, including deposit formation, corrosion, foaming and carry over, decreased heat transfer efficiency, boiler tube failure or occlusion, for example. Boiler-impurities concentration (Boiler solids concentration) is offset by withdrawing water as normal blowdown. The heat energy in the normal blowdown, however, is a major factor reducing a boiler's thermal efficiency, and therefore a blowdown rate in excess of that required to limit solids concentration should be avoided. An excessive blowdown rate also unnecessarily increases water costs.

By recycling the expelled fluid into the energy transfer system, a typical food processing facility becomes more efficient in its energy and water use. The expelled fluid is typically reasonably pure and rich in energy. Certain events can cause the expelled fluid to take on contamination levels that can result in significant problems in an energy transfer system, particularly a boiler system.

In the sugar industry, the condensate released by a multiple effect evaporator ("MEE") is an example of a typical expelled fluid. MEE condensate is relatively pure and warm. Certain events, however, can cause MEE condensate to become overly contaminated. Examples of these events include steam carry-over, foaming induced by MEE control issues, leaking of sugar thin juice into the stream, or other causes. These events are more likely to happen during operation upsets and can cause "sugar shot," which accounts for a sharp increase in contaminant levels. Contamination is generally comprised of organic salts, inorganic salts, and sucrose. If sugar shot is not timely detected, the contaminants will be recycled into the energy transfer system. The contaminants may cause the energy transfer fluid to become acidic, causing any of the well-known and well-documented problems associated with acidic boiler water. Hence, on-line detection of contamination in reuse fluid with good sensitivity and reliability is critical.

Leak detection for temperature-conditioning fluids of the food processing industry among others is disclosed in Hoots et al. (U.S. Pat. Nos. 5,304,800 and 5,416,323).

Bertin et al. (U.S. Pat. No. 5,658,798) discusses a method of monitoring contamination in a food processing stream using fluorescence. Bertin deals with detection of food contaminants that result from leaks in a food processing system. Bertin fails to disclose control methods that prevent a contaminated stream from entering an energy transfer system. Bertin also fails to disclose the precise method of detecting the contaminants.

Alfano et al. (U.S. Pat. No. 6,255,118) discusses the use of all solid-state fluorometers in industrial processes. Alfano further deals with measurement and control of additives in an energy transfer system that uses solid-state light-emitting and -detecting devices. Where Alfano may disclose certain ranges of wavelengths to be used, Alfano fails to disclose the precise method of detecting the contaminants as discussed herein.

Additionally, Hoots et al. (U.S. Pat. Nos. 5,411,889; 5,389,548; 5,435,969) teaches monitoring by fluorescence in industrial water systems, which may include water systems of the food processing industry. Yet in each of those patents, the material to be monitored is a water treatment agent such as a scale inhibitor, a corrosion inhibitor, a dispersant, a surfactant, or an anti-foaming agent. None of these three patents directly addresses the particular problem of the food processing industry as disclosed herein.

Currently, several off-line and on-line methods of sugar detection exist. The off-line methods include qualitative alpha-naphthol, sodium/potassium analyzers and molybdate ammonium/phenol sulfuric, total organic carbon (TOC), near infrared (nIR) testing. Few are able to provide on-line monitoring to contamination and are highly labor- and time-consuming. Those few that provide on-line monitoring are expensive, too sensitive, or both. Using pH and conductivity probes to monitor boiler feedwater and blowdown is also applied in some sites as on-line detection methods. However, these methods typically lack sensitivity, accuracy, and reliability.

Accordingly, there is a need for an on-line detection method. Desirably, the method will be capable of detecting impurities associated with sugar shot with sensitivity, accuracy, and reliability. More desirably, the method will be capable of diverting overly contaminated fluid from entering an energy transfer system.

SUMMARY OF THE INVENTION

The invention is a method of measuring impurities in a fluid and preventing contamination of energy transfer fluid. The fluid is expelled from a process and is used to feed an energy transfer system when the fluid is suitably pure. The constituent measured is a fluorescing impurity, the presence of which indicates the further presence of other impurities that are harmful to an energy transfer system. The method is applicable to the following food processing operations among others: meat, vegetable oil, sugar beet, sugar cane, grain, poultry, fruit, and soybean processing operations.

The invention optionally controls a fluid stream from entering an energy transfer system by measuring certain impurities associated with food processing. The impurities are measured using fluorescent light at specific wavelengths. The quantified presence of the impurities in the fluid stream can be correlated to the presence of other impurities in the fluid stream that are known to cause problems if introduced into an energy transfer system, particularly a boiler system. Once detected, the fluid stream can be diverted from entering the energy transfer system.

These and other features and advantages of the present invention will be apparent from the following detailed description, in conjunction with the appended claims.

BRIEF DESCRIPTION OF THE DRAWINGS

The benefits and advantages of the present invention will become more readily apparent to those of ordinary skill in the relevant art after reviewing the following detailed description and accompanying drawings, wherein:

FIG. 1 is a graphical display of the calibration curves derived in Example 1;

FIG. 2 is a graphical display of Field Test 1 performed in Example 2; and

FIG. 3 is a graphical display of Field Test 2 performed in Example 2.

DEFINITIONS

"Channel" refers to a combination of a fluorescence excitation wavelength paired with a fluorescence emission wavelength that is used to perform one measurement and creates the basis for a correlation of the measurement with a particular contaminant. For example, a 280 nm excitation light source and a 340 nm emission light filter is a channel that is used to perform one measurement.

"Excitation light source" refers to anything that produces fluorescent excitation light at a given wavelength or range of wavelengths. The excitation light source typically comprises a fluorescent light source such as an LED coupled with a bandpass filter at a particular wavelength; however, other devices may be used to produce excitation light at a wavelength or range of wavelengths.

"About" refers to a range of variables. When used in reference to a range of wavelengths, "about" refers to a range of wavelengths that is ±20 nm.

DETAILED DESCRIPTION OF THE INVENTION

While the present invention is susceptible of embodiment in various forms, there will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description of the Invention," relates to a requirement of the United States Patent Office, and does not imply, nor should be inferred to limit the subject matter disclosed herein.

The invention is a method of measuring impurities in a fluid and preventing contamination of energy transfer fluid. The fluid is expelled from a food processing system and is typically reused in an energy transfer system because the fluid is rich in energy. Impurities in the fluid can include fluorescing compounds, with the concentration of the fluorescing compounds correlating to a concentration of sucrose, organic salts, and inorganic salts. Sucrose, organic salts, and inorganic salts are recognized as harmful compounds when present in energy transfer systems, especially boiler systems, and should be prevented from entering said systems.

The invention shines excitation fluorescent light at specific wavelengths into the fluid that is expelled by the food processing system. One way of achieving specific wavelengths requirement is to employ filters that prevent all but the desired wavelength to pass through. When exposed to the fluorescent light of the specific wavelengths, the expelled fluid in turn emits emission fluorescent light. Only certain wavelengths of emission fluorescent light should be measured, and wavelength filters are employed to allow emission fluorescent light of only certain wavelengths to pass through to the detector. The detection allows for the quantification of the concentration of fluorescing organic impurities that are found in sugar thin juice. The measured concentration of these impurities can be correlated with the concentration of the recognized harmful compounds.

The fluorescent wavelengths employed by the invention include four channels specific to measuring the fluorescing organic impurities typically associated with sugar thin juice. Two of these impurities are tryptophan and 1,3,6,8-pyrene-tetrasulfonic acid ("PTSA"). The following two fluorescent wavelength combinations can be used to measure the concentrations of these two compounds: a) 320 nm excitation fluorescent light directed through the fluid and paired with 406 nm emission fluorescent detection; and b) 320 nm excitation fluorescent light directed through the fluid and paired with 409 nm emission fluorescent light detection. Optionally, the invention may also employ the following four channels: c) 280 nm excitation fluorescent light directed through the fluid and paired with 340 nm emission fluorescent detection; d) 365 nm excitation fluorescent light directed through the fluid and paired with 409 nm emission fluorescent light detection; e) 280 nm excitation fluorescent light directed through the fluid and paired with a turbidity detection filter; and f) 365 nm excitation fluorescent light directed through the fluid and paired with 406 nm emission fluorescent light detection. All excitation fluorescent light of the aforementioned wavelengths can be created by a fluorescent light source such as an LED, with the excitation fluorescent light being filtered at the desired wavelength. The excitation fluorescent light filtering can be accomplished using bandpass filters. Turbidity may also be detected using excitation fluorescent light at either 320 nm or 365 nm.

The detection at the aforementioned wavelengths and turbidity is also achieved using fluorescent light filtering techniques that are applied to the emission fluorescent light. The emission fluorescent light filtration at the 406 nm wavelength channels can be accomplished using bandpass filters, while the filtration at the 409 nm wavelength channels can be accomplished using longpass edge filters. A turbidity detection filter is used to detect turbidity.

The data generated by the invention is used to control the fluid from entering an energy transfer system when the fluid is deemed too rich in impurities. For instance, the invention's user can set an impurity concentration setpoint that, when exceeded, triggers a flow stopping mechanism to close. The detection may provide an input into a control system that triggers a value to close, a pump to start or stop, or any number of typical process control operations. The flow stopping mechanism stops the fluid from entering the energy transfer system, preventing the energy transfer system fluid from becoming contaminated with the exceedingly impure fluid. Preferentially, the fluid is continuously monitored and controlled while all associated processes (food processing system(s), energy transfer system(s), etc.) are continuously operational. However, one of skill in the art will appreciate that the invention is capable of being practiced in batch, continuous, as-needed, or in any other manner.

The fluid measured for fluorescing impurities is typically expelled from a food processing system. The fluid is typically water of reasonable purity that is expelled as condensate from MEEs. The food processing system may be a sugar processing plant. The condensate may contain concentrations of sucrose, organic salts, or inorganic salts. The condensate is typically collected and fed to an energy transfer system. The energy transfer system is typically a system that provides heat to the food processing system or any other operation requiring heat input. The energy transfer system typically includes a boiler.

EXAMPLES

While not intending to limit the invention to any particular embodiment other than that described in the claims, several examples are described below to allow one to better understand the invention.

Example 1

Fluorescence scans for six sets of sugar cane juice samples were performed. Six combinations of excitation and emission fluorescent light wavelength filters were used to perform the scans: 280 nm bandpass excitation filter with 340 nm bandpass emission filter ("EX280/EM340"); 280 nm bandpass excitation filter with a turbidity detection filter ("EX280/EM-T"); 320 nm bandpass excitation filter with 406 nm bandpass emission filter ("EX320/EM406"); 320 nm bandpass excitation filter with 409 nm longpass edge emission filter ("EX320/EM409"); 365 nm bandpass excitation filter with 406 nm bandpass emission filter ("EX365/EM406"); and 365 nm bandpass excitation filter with 409 nm longpass edge emission filter ("EX365/EM409"). The calibration solution for the fluorometer contained two kinds of fluorophores: 0.1 ppm tryptophan for the 280 nm channels; and 0.1 ppm PTSA for the 320 nm and 365 nm channels.

Bench-top tests were conducted to evaluate the response of the selected channels to different concentrations of sugar cane juice in order to create calibration curves. Samples were prepared by spiking deionized water with 0, 0.05%, 0.10%, 0.15%, and 0.20% of sugar thin juice and measured at the aforementioned channels. The aforementioned excitation light wavelengths were projected into the samples, with emission fluorescent light being filtered and detected by a fluorometer. Readings from the following channels were plotted as a function of percent sugar thin juice: EX280/EM340, EX320/EM406, EX320/EM409, EX365/EM409 (see FIG. 1). As shown in FIG. 1, fluorescence intensity measured from these four channels was a linear function of the sugar thin juice concentration in deionized water, even at low contamination levels (≤0.20%).

Example 2

Two separate field trials were performed on MEE condensate at two sugar plants employing the same channel configuration as in Example 1 to measure impurities in the MEE condensate. FIGS. 2 and 3 show the respective results of these field trials. The fluorometer readings were compared to analyses performed by workers of each sugar plant. These analyses employed the ammonium molybdate colorimeric method, and the fluorometer readings were comparable to the analyses.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the illustrated specific embodiments or examples is intended or should be inferred. The disclosure is intended to cover by the appended claims all such modifications as fall within the scope of the claims.

We claim:

1. A method of detecting impurities in a fluid, the fluid expelled from a process, the method comprising:
    detecting an impurity in the fluid using a fluorescence detection system, wherein the fluorescence detection system comprises at least two channels, the at least two channels comprising:
    a first channel, the first channel comprising an excitation light source having a wavelength in a range from 300 to 340 nm, and a 406 nm wavelength bandpass emission filter, and a second channel, the second channel comprising an excitation light source having a wavelength of in a range from 300 to 340 nm, and a 409 nm wavelength longpass emission filter.

2. The method of claim 1, wherein the fluorescence detection system comprises an additional channel, the additional channel comprising an excitation light source having a wavelength in a range from 345 to 385 nm, and a 409 nm wavelength longpass emission filter.

3. The method of claim 1, wherein the fluorescence detection system comprises an additional channel, the additional channel comprising an excitation light source having a wavelength in a range from 260 to 300 nm, and a 340 nm wavelength bandpass emission filter.

4. The method of claim 1, wherein the fluorescence detection system comprises an additional channel, the additional channel comprising an excitation light source having a wavelength in a range from 345 to 385 nm, and a 406 nm wavelength bandpass emission filter.

5. The method of claim 1, wherein the fluorescence detection system comprises an additional channel, the additional channel comprising an excitation light source and a turbidity detection filter.

6. A method of detecting impurities in a fluid, the fluid expelled from a process, the method comprising:
    detecting an impurity in the fluid using a fluorescence detection system, wherein the fluorescence detection system comprises at least two channels, the at least two channels comprising:
    a first channel, the first channel comprising a 320 nm wavelength excitation light source and a 406 nm wavelength bandpass emission filter, and
    a second channel, the second channel comprising a 320 nm wavelength excitation light source and a 409 nm wavelength longpass emission filter.

7. A method of regulating a fluid entering an energy transfer system, wherein a process expels the fluid, the method comprising:

detecting an impurity in the fluid using a fluorescence detection system, wherein the fluorescence detection system comprises:

a first channel, the first channel comprising a 320 nm wavelength excitation light source and a 406 nm wavelength bandpass emission filter, and a second channel, the second channel comprising a 320 nm wavelength excitation light source and a 409 nm wavelength longpass emission filter;

determining a concentration of the impurity from the detection;

comparing the concentration of the impurity to a setpoint; and providing an input into a control system, wherein the input is derived from the comparing.

8. The method of claim 7, wherein the control system prevents the fluid from entering the energy transfer system when the input indicates that the concentration of the impurity is greater than the setpoint.

9. The method of claim 7, wherein the fluorescence detection system comprises an additional channel, the additional channel comprising a 365 nm wavelength excitation light source and a 409 nm wavelength longpass emission filter.

10. The method of claim 7, wherein the fluorescence detection system comprises an additional channel, the additional channel comprising a 280 nm wavelength excitation light source and a 340 nm wavelength bandpass emission filter.

11. The method of claim 7, wherein the fluorescence detection system comprises an additional channel, the additional channel comprising a 365 nm wavelength excitation light source and a 406 nm wavelength longpass emission filter.

12. The method of claim 7, wherein the fluorescence detection system comprises an additional channel, the additional channel comprising an excitation light source and a turbidity detection filter.

13. The method of claim 7, wherein the fluid is a condensate expelled from a multiple effect evaporator.

* * * * *